United States Patent

Lantzsch

[11] 4,276,218
[45] Jun. 30, 1981

[54] PREPARATION OF DIHALOGENOVINYL-γ-BUTYROLACTONES

[75] Inventor: Reinhard Lantzsch, Leverkusen, Fed. Rep. of Germany

[73] Assignee: Bayer Aktiengesellschaft, Leverkusen, Fed. Rep. of Germany

[21] Appl. No.: 67,241

[22] Filed: Aug. 16, 1979

[51] Int. Cl.$^3$ .......................................... C07D 307/32
[52] U.S. Cl. ................................................ 260/343.6
[58] Field of Search ..................................... 260/343.6

[56] References Cited

U.S. PATENT DOCUMENTS 3,299,100  1/1967  Phillips .............................. 260/343.6

FOREIGN PATENT DOCUMENTS 2732456  1/1978  Fed. Rep. of Germany.
1503857  3/1978  United Kingdom.

OTHER PUBLICATIONS

Per D. Klemmensen et al., J. Org. Chem., vol. 44, No. 3 (1979) pp. 416–419.

*Primary Examiner*—Norma S. Milestone
*Attorney, Agent, or Firm*—Sprung, Felfe, Horn, Lynch & Kramer

[57] ABSTRACT

A process for the preparation of a dihalogenovinyl-γ-butyrolactone of the formula

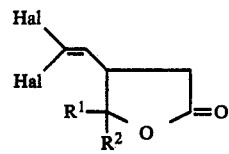

in which
Hal each independently is F, Cl or Br, and
$R^1$ and $R^2$ each independently is hydrogen or $C_{1-4}$-alkyl, or $R^1$ and $R^2$ together with the adjacent carbon atom form a cycloaliphatic ring with up to 7 carbon atoms, comprising hydrolyzing in acidic aqueous medium a compound of the formula

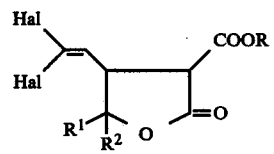

in which
R is hydrogen or $C_{1-4}$-alkyl, to form the corresponding acid and then, without isolation of the intermediate hydrolysis product, heating at 110°–120° C. to decarboxylate.

4 Claims, No Drawings

PREPARATION OF DIHALOGENOVINYL-γ-BUTYROLACTONES

The present invention relates to an unobvious process for the preparation of certain dihalogenovinyl-γ-butyrolactones, some of which are known, to certain new dihalogenovinyl-γ-butyrolactones and to intermediate for their preparation.

Dihalogenovinyl-γ-butyrolactones are valuable intermediates for the preparation of dihalogenovinylcyclopropanecarboxylic acid esters, some of which are known, which are used as insecticides. These preparative processes are the subject of Patent Application Ser. No. 879,022, filed Feb. 17, 1978, now abandoned, the disclosure of which is incorporated herein by reference.

Vinyl-substituted γ-butyrolactones and processes for their preparation have already been disclosed in German Offenlegungsschriften (German Published Specification) Nos. 2,461,525 and 2,509,576. However, the processes described in these publications are not very economical and, in addition, are limited to vinyl-substituted or dialkylvinyl-substituted γ-butyrolactones.

In addition, it has been disclosed that 4-methyl-3-(2',2'-dichlorovinyl)-γ-valerolactone is formed as a by-product in the hydrolysis of 2,2'-dimethyl-3-(2',2'-dichlorovinyl)-cyclopropane-1-carboxylic acid (see Pestic. Sci. 1974 (5) pages 792–793).

Moreover, a process for the preparation of 4-(2',2'-dihalogenovinyl)-3,3-dimethyl-γ-butyrolactones has been disclosed in German Offenlegungsschrift (German Published Specification) No. 2,623,777. However, the process, starting from dimedone, described in this publication can only be carried out in an uneconomical manner and, in addition, does not lead to the desired 3-dihalogenovinyl-γ-butyrolactones.

In Application Ser. No. 879,022 supra and Application Ser. No. 053,656 filed June 29, 1979, now pending, the disclosures of which are incorporated herein by reference, there is disclosed a process for the preparation of a dihalogenovinyl-γ-butyrolactone of the formula

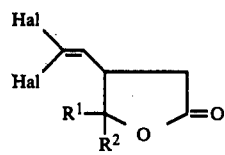

(I)

in which
Hal represents F, Cl or Br, the Hal atoms being identical or different,
$R^1$ and $R^2$, which may be identical or different, each represents hydrogen or $C_{1-4}$-alkyl, or $R^1$ and $R^2$, together with the adjacent carbon atom, form a cycloaliphatic ring with up to 7 carbon atoms,
in which a compound of the general formula

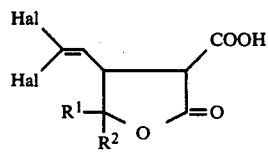

(II), in which Hal, $R^1$ and $R^2$ have the meanings stated above, is heated, optionally in the presence of a diluent, or (1.2) a compound of the general formula

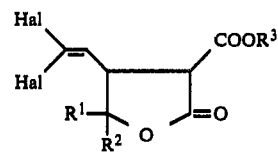

is hydrolyzed and then decarboxylated.

In accordance with the present invention the decarboxylation is effected at a temperature of about 110° to about 120° C. and preferably about 115° C.

In accordance with another aspect of the invention the hydrolysis reaction mass can be directly heated to effect decarboxylation without intermediate isolation. Suitable acids are the inexpensive mineral acids, actually sulfuric or phosphoric acids. The concentration may vary widely, but about 10 to 85%, especially about 20 to 40% by weight based on water plus acid, is especially useful.

Surprisingly the use of decarboxylation temperatures of about 115° C. gives results far superior to temperatures substantially higher or lower, e.g. 110° or 130° C.

The invention will be further described in the following example:

EXAMPLE (a) 500 g ethanol are added to 360 g of a 30% strength industrial sodium methylate solution. 320 g of malonic acid diethyl ester are added dropwise over 30 minutes and the mixture is heated to 35° C. 334 g 2,2-dimethyl-3-(2',2'-dichlorovinyl)-oxirane are added, the temperature rising to 40° C., and then the reaction mixture is kept at 40° C. for five hours. The product at this stage is 4-methyl-3-(2',2'-dichlorovinyl)-γ-valerolactone-2-carboxylic acid ethyl ester. After cooling, 1000 g of 25 weight % sulfuric acid is added and the solvent mixture is brought to 115° C. under normal pressure with removal of distillate. The mixture is kept at this temperature for 4-5 hours without further distillation and is then allowed to cool. After diluting with water the mixture is filtered, washed with light petroleum and dried.

Yield: 294 g of 4-methyl-3-(2',2'-dichlorvinyl)-γ-valerolactone of melting point 112° C., corresponding to a yield of 70.5% based on 2,2-dimethyl-3-(2',2'-dichlorovinyl)-oxirane.

(b) If the process of (a) is repeated except that the solvent mixture is brought to and maintained at 100° C., the yield of lactone is <5%.

(c) If the process of (a) is repeated except that the solvent mixture is brought to and maintained at 130° C., the yield of lactone is 59%.

It will be appreciated that the instant specification and examples are set forth by way of illustration and not limitation, and that various modifications and changes may be made without departing from the spirit and scope of the present invention.

What we claim is:
1. In the preparation of a dihalogenovinyl-γ-butyrolactone of the formula

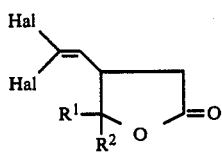

in which
- Hal each independently is F, Cl or Br, and
- $R^1$ and $R^2$ each independently is $C_{1-4}$-alkyl, or $R^1$ and $R^2$ together with the adjacent carbon atoms form a cycloaliphatic ring with up to 7 carbon atoms, by hydrolyzing to the corresponding acid a compound of the formula

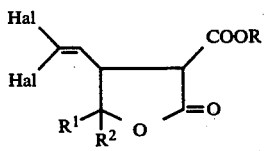

in which R is $C_{1-4}$-alkyl, and then decarboxylating, the improvement which comprises effecting hydrolysis in acidic aqueous solution and heating the hydrolysis mass, without isolation of the intermediate hydrolysis product, at a temperature of about 110° to 120° C.

2. A process according to claim 1, in which the acidic aqueous medium comprises aqueous sulfuric acid and heating is effected at about 115° C.

3. A process according to claim 2, wherein the starting material is produced by condensing

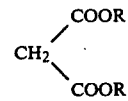

with an oxirane of the formula

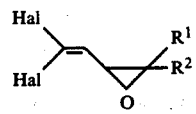

in the presence of a base, hydrolysis being effected by adding the sulfuric acid to the condensation reaction mass without isolation.

4. A process according to claim 3, in which Hal is chlorine, $R^1$ and $R^2$ is methyl.

* * * * *

UNITED STATES PATENT AND TRADEMARK OFFICE
CERTIFICATE OF CORRECTION

PATENT NO. : 4,276,218
DATED : June 30, 1981
INVENTOR(S) : Reinhard Lantzsch

It is certified that error appears in the above—identified patent and that said Letters Patent is hereby corrected as shown below:

Column 2, line 28 "110°" should be "100°"

Signed and Sealed this

Twenty-ninth Day of September 1981

[SEAL]

Attest:

GERALD J. MOSSINGHOFF

Attesting Officer     Commissioner of Patents and Trademarks